(12) United States Patent
Jean et al.

(10) Patent No.: US 10,920,606 B2
(45) Date of Patent: Feb. 16, 2021

(54) METHOD AND SYSTEM FOR DIAGNOSING A CONDITION OF AN ENGINE USING LUBRICATING FLUID ANALYSIS

(71) Applicant: PRATT & WHITNEY CANADA CORP., Longueuil (CA)

(72) Inventors: Maurice Jean, Boucherville (CA); Daniel Meilleur, Boucherville (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 0 days.

(21) Appl. No.: 16/690,690

(22) Filed: Nov. 21, 2019

(65) Prior Publication Data

US 2020/0102851 A1 Apr. 2, 2020

Related U.S. Application Data

(63) Continuation of application No. 14/962,389, filed on Dec. 8, 2015, now Pat. No. 10,519,800.

(51) Int. Cl.
| | |
|---|---|
| *F01D 21/00* | (2006.01) |
| *G16C 20/20* | (2019.01) |
| *F01D 25/18* | (2006.01) |
| *G01M 15/14* | (2006.01) |
| *G01N 15/10* | (2006.01) |

(52) U.S. Cl.
CPC ......... *F01D 21/003* (2013.01); *F01D 25/18* (2013.01); *G01M 15/14* (2013.01); *G01N 15/10* (2013.01); *G16C 20/20* (2019.02); *F05D 2220/323* (2013.01); *F05D 2260/98* (2013.01)

(58) Field of Classification Search
CPC .................................................. F01D 21/003
See application file for complete search history.

(56) References Cited

U.S. PATENT DOCUMENTS

| | | | |
|---|---|---|---|
| 3,751,661 A | 8/1973 | Packer et al. | |
| 3,981,584 A | 9/1976 | Guymer | |
| (Continued) | | | |

FOREIGN PATENT DOCUMENTS

| | | | |
|---|---|---|---|
| EP | 0672243 B1 | 3/2000 | |
| EP | 2485037 B1 | 5/2015 | |
| (Continued) | | | |

OTHER PUBLICATIONS

United State Patent and Trademark Office, Office Action dated Nov. 30, 2017 re: U.S. Appl. No. 14/962,389.
(Continued)

*Primary Examiner* — Manuel A Rivera Vargas
(74) *Attorney, Agent, or Firm* — Norton Rose Fulbright Canada LLP

(57) ABSTRACT

Methods and systems for diagnosing a condition of an engine based on lubrication fluid analysis are disclosed. One embodiment of the methods comprises: receiving input data representative of a respective geometric parameter and a respective chemical composition for a plurality of particles filtered from a sample of fluid obtained from the engine; generating data representative of a mass of material of a chemical composition category in one or more of the particles; comparing the mass of material of the chemical composition category with reference data; and generating output data representative of a diagnosis of the condition of the engine.

15 Claims, 7 Drawing Sheets

(56) References Cited

U.S. PATENT DOCUMENTS

| | | | |
|---|---|---|---|
| 5,517,427 | A | 5/1996 | Joyce |
| 5,537,336 | A | 7/1996 | Joyce |
| 5,586,161 | A | 12/1996 | Russell et al. |
| 5,817,928 | A | 10/1998 | Garvey, III et al. |
| 5,982,847 | A | 11/1999 | Nelson |
| 6,435,013 | B1 | 8/2002 | Rodriguez et al. |
| 6,473,677 | B1 | 10/2002 | Hershey et al. |
| 6,598,464 | B1 | 7/2003 | Rossi |
| 6,643,570 | B2 | 11/2003 | Bangert et al. |
| 6,859,517 | B2 | 2/2005 | Wilson et al. |
| 7,184,515 | B2 | 2/2007 | Wilson |
| 7,523,615 | B2 | 4/2009 | Singh et al. |
| 7,634,913 | B2 | 12/2009 | Singh et al. |
| 7,689,368 | B2 | 3/2010 | Douglas |
| 7,745,382 | B2 | 6/2010 | Sloan |
| 8,522,604 | B2 | 9/2013 | Zhe et al. |
| 8,607,621 | B2 | 12/2013 | Verdegan |
| 8,676,436 | B2 | 3/2014 | Raimarckers et al. |
| 8,805,624 | B2 | 8/2014 | Uluyol |
| 8,862,433 | B2 | 10/2014 | Yerramalla et al. |
| 9,032,803 | B2 | 5/2015 | Griffaton |
| 9,244,042 | B2 | 1/2016 | Rank |
| 9,897,582 | B2 | 2/2018 | Jean et al. |
| 2005/0002030 | A1 | 1/2005 | Kolp |
| 2005/0043901 | A1* | 2/2005 | Hayzen ............... G01N 15/02 702/26 |
| 2010/0138132 | A1 | 6/2010 | Apps et al. |
| 2011/0095190 | A1 | 4/2011 | Kommareddy et al. |
| 2012/0330499 | A1 | 12/2012 | Scheid et al. |
| 2013/0132034 | A1 | 5/2013 | Wilson |
| 2014/0121994 | A1* | 5/2014 | Jean ..................... G06F 15/00 702/27 |
| 2014/0324363 | A1 | 10/2014 | Reinman |
| 2015/0047419 | A1 | 2/2015 | Cao et al. |
| 2016/0093481 | A1 | 3/2016 | Bick et al. |
| 2016/0370341 | A1 | 12/2016 | Jean et al. |
| 2017/0159485 | A1 | 6/2017 | Jean et al. |

FOREIGN PATENT DOCUMENTS

| | | |
|---|---|---|
| JP | 10330779 | 12/1998 |
| WO | 2008013597 | 1/2008 |
| WO | 2015025160 A1 | 2/2015 |

OTHER PUBLICATIONS

Norton Rose Fulbright Canada LLP, Response dated Feb. 27, 2018 to Office Action dated Nov. 30, 2017 re: U.S. Appl. No. 14/962,389.
United State Patent and Trademark Office, Office Action dated Jun. 22, 2018 re: U.S. Appl. No. 14/962,389.
Norton Rose Fulbright Canada LLP, Response dated Aug. 22, 2018 to Office Action dated Jun. 22, 2018 re: U.S. Appl. No. 14/962,389.
United State Patent and Trademark Office, Office Action dated Nov. 30, 2018 re: U.S. Appl. No. 14/962,389.
Norton Rose Fulbright Canada LLP, Response dated Feb. 28, 2019 to Office Action dated Nov. 30, 2018 re: U.S. Appl. No. 14/962,389.
United State Patent and Trademark Office, Office Action dated Jun. 10, 2019 re: U.S. Appl. No. 14/962,389.
Norton Rose Fulbright Canada LLP, Response dated Aug. 12, 2019 to Office Action dated Jun. 10, 2019 re: U.S. Appl. No. 14/962,389.
Canadian Intellectual Proprty Office, Office Action dated May 14, 2019 re: Application No. 2,927,683.
United States Patent and Trademark Office, Office Action, dated Apr. 4, 2018, 23 pages, U.S. Appl. No. 15/137,841.
Canadian Intellectual Property Office, Examiner's Requisition dated May 4, 2018 re: Canadian patent application No. 2,927,683.
Norton Rose Fulbright Canada LLP, Canadian Intellectual Property Office, Response dated Jan. 16, 2018 to Examiner's Requisition dated Jul. 17, 2017 re: Canadian patent application No. 2,927,683.
Canadian Intellectual Property Office, Examiner's Requisition dated Jul. 17, 2017 re: Canadian patent application No. 2,927,683.
United States Patent and Trademark Office, Office Action dated Feb. 9, 2017 re: U.S. Appl. No. 13/661,181.
United States Patent and Trademark Office, Response dated May 8, 2017 to Office Action dated Feb. 9, 2017 re: U.S. Appl. No. 13/661,181.
United States Patent and Trademark Office, Supplementary Response dated Jun. 2, 2017 to Office Action dated Feb. 9, 2017 re: U.S. Appl. No. 13/661,181.
European Patent Office; Extended European Search Report dated Jan. 3, 2017 re: European Patent Application No. 16191213.4.
Levi et al., Failure Analysis and Condition Monitoring of an Open-Loop Oil System Using Ferrography, Tribology Letters, May 12, 2009, pp. 17-29, vol. 36, No. 1, Kluwer Academic Publishers= Plenum Publishers, NE.
United States Patent and Trademark Office, Office Action dated Sep. 20, 2016 re: U.S. Appl. No. 13/661,181.
Norton Rose Fulbright Canada LLP, Response to U.S. Office Action dated Sep. 20, 2016 re: U.S. Appl. No. 13/661,181.
Norton Rose Fulbright Canada LLP, Response to U.S. Office Action dated Mar. 28, 2016 re: U.S. Appl. No. 13/661,181.
United States Patent and Trademark Office, Office Action dated Mar. 28, 2016 re: U.S. Appl. No. 13/661,181.
Om Prakash Sondhiya et al., Wear Debris Analysis of Automotive Engine Lubricating Oil Using by Ferrography, IJEIT, Nov. 2012, pp. 46-54, vol. 2, Issue 5, ISSN: 2277-3754.
Norton Rose Fulbright Canada LLP, Response to U.S. Office Action dated Jul. 2, 2015 re: U.S. Appl. No. 13/661,181.
Noria Corporation, "Using Electron Microscopy in Oil Analysis Applications—Comparing SEM to TEM", 6 pages. http://www.machinerylubrication.com/Read/698/electron-microscopy-sem-oil.
Golden, "The Determination of Iron in Used Lubricating Oil", Applied Spectroscopy, vol. 25, No. 6, Nov./Dec. 1971, pp. 668-671.
Herguth et al., "Applications of Scanning Electron. Microscopy and Energy Dispersive. Spectroscopy (SEM/EDS). To Practical Tribology Problems", Herguth Laboratories, 9 pages. http://www.herguth.com/technical/sem.pdf.
Vahaoja, "Oil Analysis in Machine Diagnostics", Acta Universitatis Ouluensis: A Scientiae Rerum Naturalium, vol. 458, University of Oulu, 2006, 80 pages.
Whitlock, "X-ray Methods for Monitoring Machinery Condition", Advances in X_ray Analysis, vol. 40, proceedings of the 45th Annual Denver X-ray Conferences, Aug. 1996, 12 pages.
Lukas et al., "Rotrode Filter Spectroscopy, Does It have a Place in Commercial or Military Oil Analysis Laboratory", Spectro Incorporated, Littleton, Massachusetts, 7 pages. http://protechanalytical.com/PDF%20files/RFS-4_98-1.pdf.
Eisentraut et al., "Spectrometrix Oil Analysis: Detecting Engine Failures Before They Occur", Analytical Chemistry, vol. 56, No. 9, Aug. 1984, pp. 1086A-1094A.
Farrant et al., "Effective Condition Monitoring of Aero-Engine Systems Using Automated SEM/EDX and New Diagnostic Routines", 1998, 14 pages.
Amsoil, "Correlation between particle size and engine wear", Technical service bulletin, A-F-Jul. 25, 2007, 3 pages. https://www.amsoil.com/techservicesbulletin/Aftermarket/TSB-AF-2007-07-25%20Oil%20filters%20Particle%20Size%20and%20Engine%20Wear.pdf.
Scientific and Techinal Information Center, "Search Report", STIC Database Tracking No. 487946, Jun. 19, 2014, 24 pages.
United States Patent and Trademark Office, Office Action dated Jul. 2, 2015 re: U.S. Appl. No. 13/661,181.
Canadian Intellectual Proprty Office, Office Action dated Feb. 27, 2020 re: Application No. 2,927,683.
English translation of Japan patent document No. JP10330779 dated Dec. 15, 1998, https://patents.google.com/patent/JPH10330779A/en?oq=JP10330779, accessed on May 12, 2020.

* cited by examiner

METHOD AND SYSTEM FOR DIAGNOSING A CONDITION OF AN ENGINE USING LUBRICATING FLUID ANALYSIS

CROSS REFERENCE TO RELATED APPLICATIONS

This application is a continuation of U.S. patent application Ser. No. 14/962,389 filed on Dec. 8, 2015, the contents of which are hereby incorporated by reference.

TECHNICAL FIELD

The disclosure relates generally to engine diagnostics and more particularly to methods and systems for diagnosing engine conditions using oil (or other lubricant) analysis.

BACKGROUND OF THE ART

The analysis of engine oil or other lubricant for the purpose of identifying premature component wearing has been performed for several decades using optical atomic spectroscopy (e.g., atomic emission spectroscopy (AES), as well as its predecessor that has been in use as a field monitoring method, atomic absorption spectroscopy (AAS)). This technology has been the basis for the military aviation's Spectroscopic Oil Analysis Program (SOAP). However, this technology can sometimes lack of repeatability among different equipment and does not consider particles greater than 5 µm in diameter. Furthermore, SOAP typically uses optical atomic spectroscopy, which is an elemental analysis of the total oil sample and typically does not characterize individual particles in the sample.

Rotrode Filter Spectroscopy has been introduced in 1980 and it was commercialized by Spectro Incorporated (Littleton, Mass.). The method focuses mainly on the analysis of large particles in the oil and has proven to be effective to establish the source of wear material in a system already generating wear material [1].

Scanning electron microscope (SEM) equipped to perform X-ray spectroscopy has been used to characterize individual particles [2] for wear mode indicators. However, SEM has been considered to be unsuitable for routine monitoring of machine condition, for example as reported in Whitlock [3].

SUMMARY

In one aspect, the disclosure describes a computer-implemented method for diagnosing a condition of an engine, the method comprising:

receiving input data representative of a respective geometric parameter and a respective chemical composition for a plurality of particles filtered from a fluid sample obtained from the engine;

using one or more data processors:

from the input data, generating data representative of a mass of material of a chemical composition category in one or more of the particles;

comparing the mass of material of the chemical composition category in the one or more particles with reference data; and based on the comparison, generating output data representative of a diagnosis of the condition of the engine.

In another aspect, the disclosure describes a method for diagnosing a condition of a gas turbine engine, the method comprising:

using a plurality of particles filtered from a sample of used lubricating fluid obtained from the gas turbine engine, generating input data representative of a respective geometric parameter and a respective chemical composition for each of the plurality of particles;

using the input data, generating data representative of a cumulative mass of material of a chemical composition category in the plurality of particles;

comparing the cumulative mass of material of the chemical composition category with reference data; and based on the comparison, generating output data representative of a diagnosis of the condition of the engine.

In some example aspects, the present disclosure provides a system for fluid analysis, the system may include a processor and a memory containing machine-readable instructions for execution by the processor, the machine-readable instructions causing the processor to carry out the methods described herein.

In some example aspects, the present disclosure provides a non-transitory computer-readable medium or media embodying computer-executable instructions configured for causing one or more processors to carry out the methods described herein.

Further details of these and other aspects of the subject matter of this application will be apparent from the detailed description and drawings included below.

DESCRIPTION OF THE DRAWINGS

Reference is now made to the accompanying drawings, in which.

DETAILED DESCRIPTION

Figure 1:
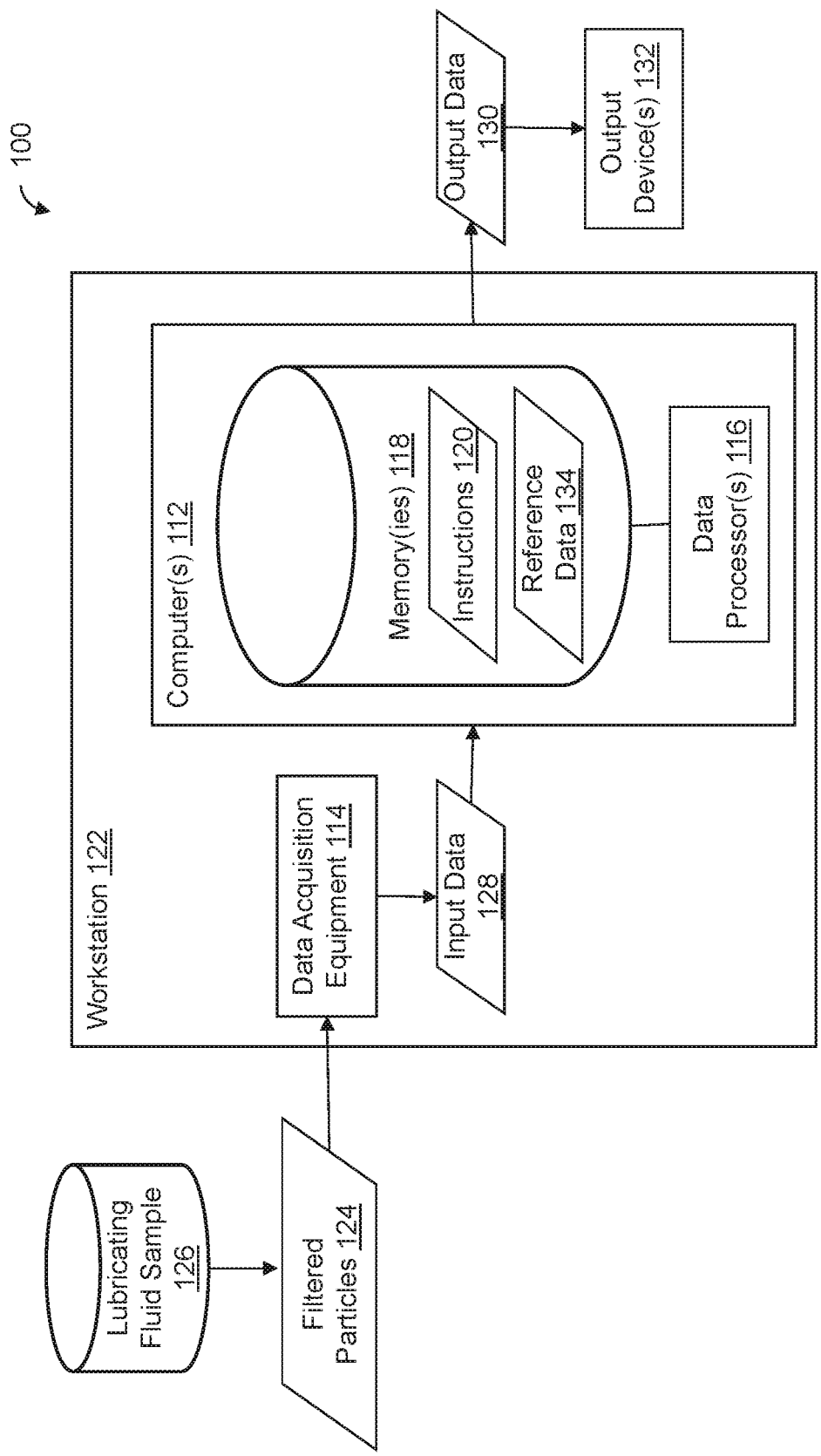
FIG. 1 is a schematic diagram of an exemplary system for diagnosing a condition of an engine such as a gas turbine engine.

The present disclosure relates to engine diagnostics using lubricating fluid analysis. In various aspects disclosed herein, such lubricating fluid analysis may use chemical composition of particles as well as geometric parameters (e.g., size and shape) and/or mass of particles for use in diagnosing a condition of an engine.

Recently developed engines, such as gas turbine engines for aircraft applications, may produce debris (e.g., metallic debris) in oil samples at a levels of concentration and at particle sizes below the operating zone of conventional oil analysis techniques. However, the analysis of such debris may still be useful in diagnosing conditions of such engines and failure prediction. For example, SOAP typically requires debris to be present on the order of parts per million (ppm) however, debris at the parts per billion (ppb) level may also be of interest for engine diagnostics.

Oil analysis has been performed for predictive maintenance (e.g., on engines) for more than fifty years but has limited capability in detecting abnormal behavior early in the process. For example, using conventional techniques, failure is typically detected only hours before a problem occurs, resulting in the need for the engine operator to submit an oil sample at short time intervals (e.g., every 10 to 50 hours) to have a chance to capture the indication of failure before the actual failure occurs. Such a high frequency of sampling may not be practical or economical for an aircraft operator.

Considering the direct and indirect costs of any engine failure and unplanned engine removal, there is a need for methods and systems that may be able to predict failure sufficiently in advance, in order for the appropriate tasks (e.g., corrective action), such as maintenance and/or decommissioning, to be scheduled and carried out.

One conventional approach for monitoring engine material wear is to perform an analysis on particles extracted from the engine filter; where the extracted particles are then analyzed by SEM. This method is relatively costly because the engine filter is typically not reused. Further, such method may not be practical considering that removing the engine filter may be time consuming. For such reasons, among others, filter analysis typically is not performed frequently and is mainly used to monitor engines already identified as potentially behaving abnormally. Filter analysis typically is not suitable for routine monitoring of engines.

Another method is to analyze particles collected from the oil by a magnetic drain plug where the magnetic particles collected by the drain plug are removed and analyzed.

The disclosure describes methods and systems for engine diagnostics (e.g., failure prediction) using oil or other lubricating fluids. In various aspects, for example, the disclosure describes methods and systems for failure prediction using analysis of particles obtained (e.g., filtered) from oil samples, such as from gas turbine engines.

In various aspects and examples, the disclosed methods and systems may allow for analysis of engine oil (or other lubricant) samples in order to detect abnormal behavior (e.g., wear mechanisms) without having to remove the engine filter. The disclosed methods and systems may be referred to as "Pratt & Whitney Canada/Complete Oil Analysis Technology" (PWCOAT).

The filtering of the particles from an oil sample obtained from the engine may provide an indication of the wear mechanism(s) active at the time the sample is collected instead of an indication of the wear mechanisms that were active at some time in the past since the fluid filter of the engine was last replaced or since particles from the magnetic drain plug were last collected. Oil samples may be collected at intervals to monitor the status of a wear mechanism of interest in order to determine whether the wear mechanism is progressing or subsiding in order to determine whether some corrective action is required. In comparison with the oil filter method, the use of an oil sample may permit smaller particles to be considered in the diagnosis as opposed to being limited to a range of particle sizes captured by the filter. In comparison with the magnetic drain plug method, the use of a fluid sample may permit for both magnetic and/or non-magnetic (e.g., aluminum) particles to be considered in the diagnosis as opposed to being limited to only magnetic particles that would be captured by the magnetic plug of the engine.

Particles filtered from a fluid sample can provide information regarding wear mechanisms that are currently active at the time the sample is obtained instead of those that were active at some point in the past and which may or may not still be active. In other words, the particles can provide a snapshot of the wear mechanism(s) active at the time when the particles are still suspended in the fluid instead of having been collected by a fluid filter of the engine or by a magnetic drain plug of the engine.

Accordingly, the disclosed methods and systems may be based on the analysis of relatively small particles in oil that typically are not captured by a conventional 30 μm porosity fluid filter of the engine. By extending the oil analysis to include smaller particles, the disclosed methods and systems may provide better understanding of engine behavior using a relatively small oil sample. For example, it has been estimated that there are, on average, about one thousand particles sized between 0.5 μm to 30 μm per ml of a typical sample, which can be analyzed to predict engine behavior and which typically are not considered in conventional filter analysis.

In some embodiments, the disclosed methods and systems may thus provide diagnostic and analytical tools based on analysis of particles in fluids, such as engine oil or other lubricants and may provide advance detection of premature wear on specific engine parts and/or detection of failure mechanisms. In some embodiments, the disclosed methods and systems may be suitable for failure prediction for gas turbine engines operating in the field. The disclosed methods and systems may be used for prediction of other wear events including prediction of events other than failure using analysis of any suitable lubricating fluid of the engine. For example, the disclosed methods and systems may be used to identify any contaminants that have been introduced into a lubricating system (e.g., by usage in abnormal conditions or by a problem during maintenance). The disclosed methods and systems may also be used to detect any abnormal behavior of an engine component in contact with a lubrication fluid system, for example.

In various embodiments, the methods and systems disclosed herein may make use of methods, steps and components of systems described in US Patent Publication No. 2014/0121994 A1, which is incorporated herein by reference in its entirety.

FIG. 1 is a schematic diagram of an exemplary system 100 for diagnosing a condition of an engine such as a gas turbine engine and which uses a fluid for lubricating some of its components such as bearings. System 100 may comprise one or more computer(s) (referred hereinafter as "computer 112") and suitable data acquisition equipment 114 of known or other type. Computer 112 may comprise one or more data processors 116 which may be any programmable data processing apparatus of known or other type, or other devices to cause a series of operational steps to be performed by computer 112 or other device(s) to produce one or more computer-implemented methods.

Computer 112 may also comprise one or more memories (referred hereinafter as "memory 118"), which may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Memory 118 may comprise any storage means (e.g. devices) suitable for retrievably storing machine-readable instructions 120 executable by data processor 116. Memory 118 may comprise tangible, non-transitory medium.

Computer 112 and data acquisition equipment 114 may be considered part of an (e.g., SEM) workstation 122. Accordingly, data acquisition equipment 114 may comprise an SEM and other related devices, although any other suitable devices/methods for extracting the relevant information from particles 124 filtered from lubricating fluid sample 126 may be used. In some embodiments, data acquisition equipment 114 may comprise an SEM and an X-Ray Fluorescence (XRF) detector for carrying out particle analysis. For example, data acquisition equipment 114 may comprise an automated SEM, such as that from Aspex Corporation. In some embodiments, the automated SEM may not require the presence of a human to select the particle(s) 124 that will be analyzed. In some embodiments, software and/or hardware included in workstation 122 may automatically recognize the presence of a particle 124 and may then automatically move a stage and/or an electron beam to the particle(s) 124 on which to perform the analysis.

System 100 may be used to conduct analysis of particles 124 filtered from lubricating fluid sample 126. Data acquisition equipment 114 may be used to analyze filtered particles 124 and generate input data 128. Input data 128 may be processed using computer 112 according to instructions 120 in order to generate output data 130. In some embodiments, output data 130 may be representative of a diagnosis of the condition of the engine and may be delivered to a user of system 100 or other authorized party via output device(s) 132 (e.g., one or more screens and/or printers) for displaying and/or otherwise providing a report of the result(s) of the diagnosis. System 100 may include one or more input devices (e.g., keyboard and mouse) for receiving user input, as well as one or more data ports and/or communication ports for receiving and/or transmitting data (e.g., wirelessly or through wired connections) from/to other processors, systems and/or devices. Processing of input data 128 by computer 112 may make use of reference data 134 for comparison purpose. It is understood that processing of input data 128 may be performed using one or more processors external to workstation 122.

Figure 2:
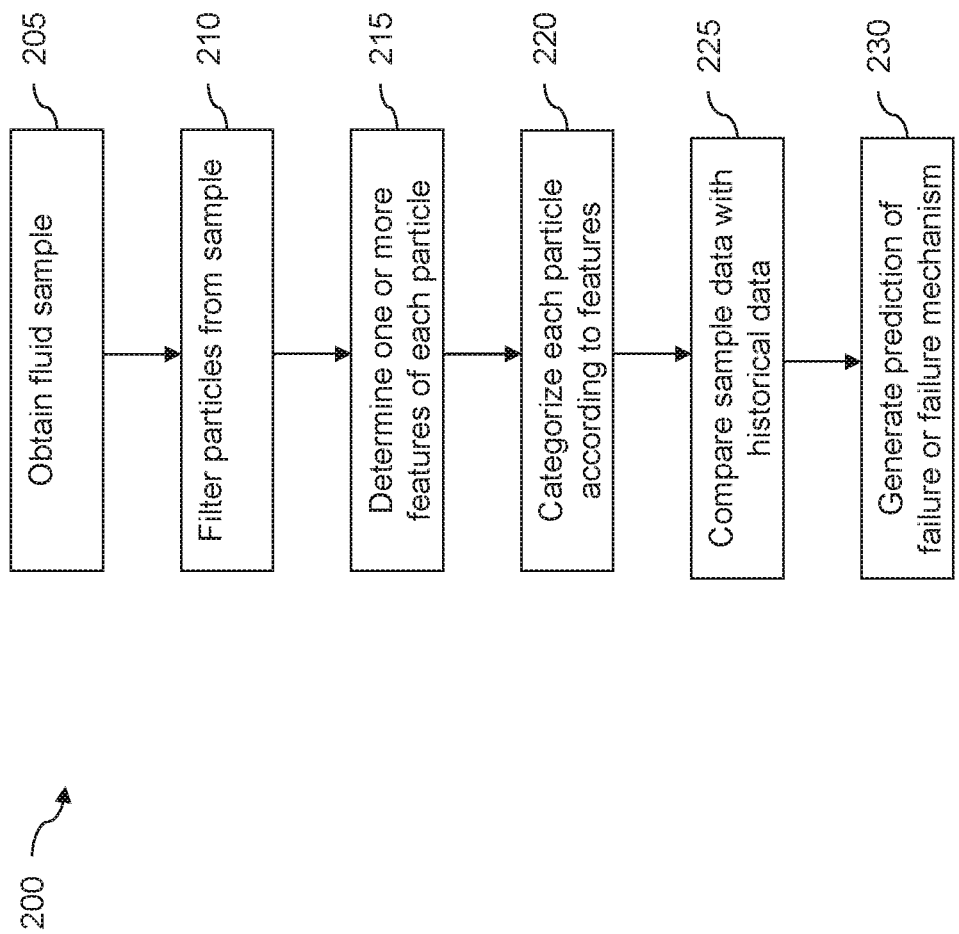
FIG. 2 is a flowchart illustrating an exemplary method for failure prediction using fluid analysis.

FIG. 2 is a flowchart illustrating an exemplary method 200 for diagnosing a condition (e.g., predicting a failure) of an engine using analysis of fluid sample 126, such as engine oil or other lubricant of the engine. Method 200 may be carried out entirely or in part using system 100 based on instructions 120. In some embodiments, depending on the configuration of system 100, some or all of method 200 may be automated (e.g., computer-implemented).

At 205, fluid sample 126 (e.g., an oil or other lubricant sample from an aircraft engine) is obtained. In the example of an oil sample from an aircraft engine, fluid sample 126 may be collected by maintenance personnel of the associated aircraft operator. Accordingly, fluid sample 126 may comprise a relatively small volume of fluid extracted from a relatively larger source of fluid of the engine. In some embodiments, more than one sample 126 may be collected from the engine. In some embodiments, a relatively small amount of oil (e.g., 25 ml or less) may be sufficient. The quantity of oil obtained may be selected in order to obtain a desired number of particles 124 for analysis. For example, it may be known or expected that a particular type of engine should have a certain density of particles in the oil after a certain number of operating hours. Accordingly, the volume of the fluid sample 126 obtained may thus be determined in order to obtain at least 1000 particles 124, for example. The frequency of sampling may be determined based on the flight/operating hours per year, the maturity of the engine, the typical behavior of the engine type and/or the history of unscheduled engine removal for that engine type, for example. The sample 126 may be obtained and prepared using any suitable known or other method.

At 210, sample 126 is filtered using any suitable known or other method to obtain particles 124 from the fluid sample 126. For example, a collected fluid sample 126 may be filtered using a very fine filter, such as a 0.22 µm filter, in order to filter out even very small particles 124 (e.g., particles sized as small as 0.5 µm in diameter or smaller). Using such a filter, a fluid sample 126 of about 25 ml may be sufficient to produce a surface sample of particles 124 of about 16 mm in diameter and suitable for data acquisition via workstation 122 for example. The particles 124 obtained may range in size from about 0.5 µm to about 1600 µm, for example, although smaller or larger particles 124 may also be obtained and used in method 200.

The volume of fluid sample 126 used and the size of the sample of particles 124 prepared may vary according to the number of particles 124 in the fluid sample 126. The volume of fluid sample 126 that is used may be determined based on the type of engine and/or the expected normal levels of particles in the oil. In some embodiments, the density of particles 124 of the surface sample of particles may be about 500 particles 124 per $mm^2$, which may be the maximum density that can be used, to reduce or avoid the likelihood of overlapping particles 124. It may be useful to reduce or avoid overlapping particles since two or more particles that overlap with each other may be incorrectly identified as one large particle, which may lead to incorrect identification and elemental analysis. For example, depending on the density of the sample of particles 124, about 5-10% of particles 124 analyzed may not be identifiable typically due to overlapping and such particles 124 may consequently be excluded from the analysis. In some embodiments, this exclusion rate may be acceptable.

At 215, some or all particles 124 filtered from fluid sample 126 are analyzed using data acquisition equipment 114 to acquire input data 128 from particles 124. Input data 128 may comprise one or more geometric parameters (e.g., shape, size, volume, one or more dimensions) and/or chemical composition information (e.g., element identification, alloy identification, material type) for each particle 124 analyzed. The one or more geometric parameters and the chemical composition may be acquired substantially automatically or semi-automatically depending on the configuration of workstation 122. For example, in some embodiments, data acquisition equipment 114 may be at least partially controlled by computer 112. Any other suitable equipment may be used to generate input data 128.

In some embodiments, a subset of the particles 124 (e.g., 10% or less) may be analyzed and may be sufficient to provide a good representation of the sample of particles 124 as a whole. For example, input data 128 acquired for the subset may be normalized to reflect/estimate the results for the whole sample of particles 124. The analysis of a subset of particles 124 may reduce processing time.

For an average fluid sample 126, about 1500 to 2000 particles 124 may be analyzed. Suitable image analyzer software, such as those conventionally used with SEM, may be used to collect data about particle characteristics and/or composition. Analysis of each particle 124 may produce a respective set of data for each particle 124. For example, in some embodiments, there may be up to 70 data points associated with each particle 124 for representing the various features of the particle 124 (e.g., size, shape and composition among others). The total number of data points obtained from analysis of a single sample may be significantly greater than in conventional oil analysis techniques.

Input data 128 obtained from this analysis may be further processed in order to account for any measurement error and/or the possible presence of contamination. This further processing may include categorizing the particles 124 as described below.

At 220, each particle 124 may be categorized based on the determined features (e.g., geometric parameter and/or chemical composition). The particles 124 may be categorized in different categories, which may be defined according to one or more of: chemical composition categories (e.g., elemental and/or alloy composition), geometric parameters (e.g., size, morphology) and mass. For example, morphology of a particle 124 may be determined by calculating an aspect ratio for the particle 124 (e.g., length to width ratio, for example, where a ratio close to 1 may indicate the particle 124 is close to having a spherical shape while a larger value, such as 10, may indicate that the particle 124 is close to a long fiber shape). For example, particles may be classified in categories such as "Environmental", "Metallic", "Non-metallic", "Plating", or "Miscellaneous", among others. Each particle 124 may be further categorized into sub-category levels. As an example, the "Metallic" category may have a level 1 sub-category of "Copper", within which may be level 2 sub-categories of "Bronze" and "Brass". In some embodiments, five levels of decisions may be used to categorize each particle 124 into a specific level (e.g., metallic, copper, bronze, leaded bronze or machining chip). Categorization of particles 124 may be based on, for example, the absolute chemical composition, the ratio of some elements, the correlation between a specific standard and particle 124, the size of particle 124, the shape of particle 124 and/or the mass of particle 124 or of some element(s) contained in particle 124. Categories may be defined according to different alloy compositions, association with one specific manufacturing process and/or association with one particular source (e.g., engine component), for example. Categories may also be defined by the elemental composition or single material of the particles 124.

Figure 3:
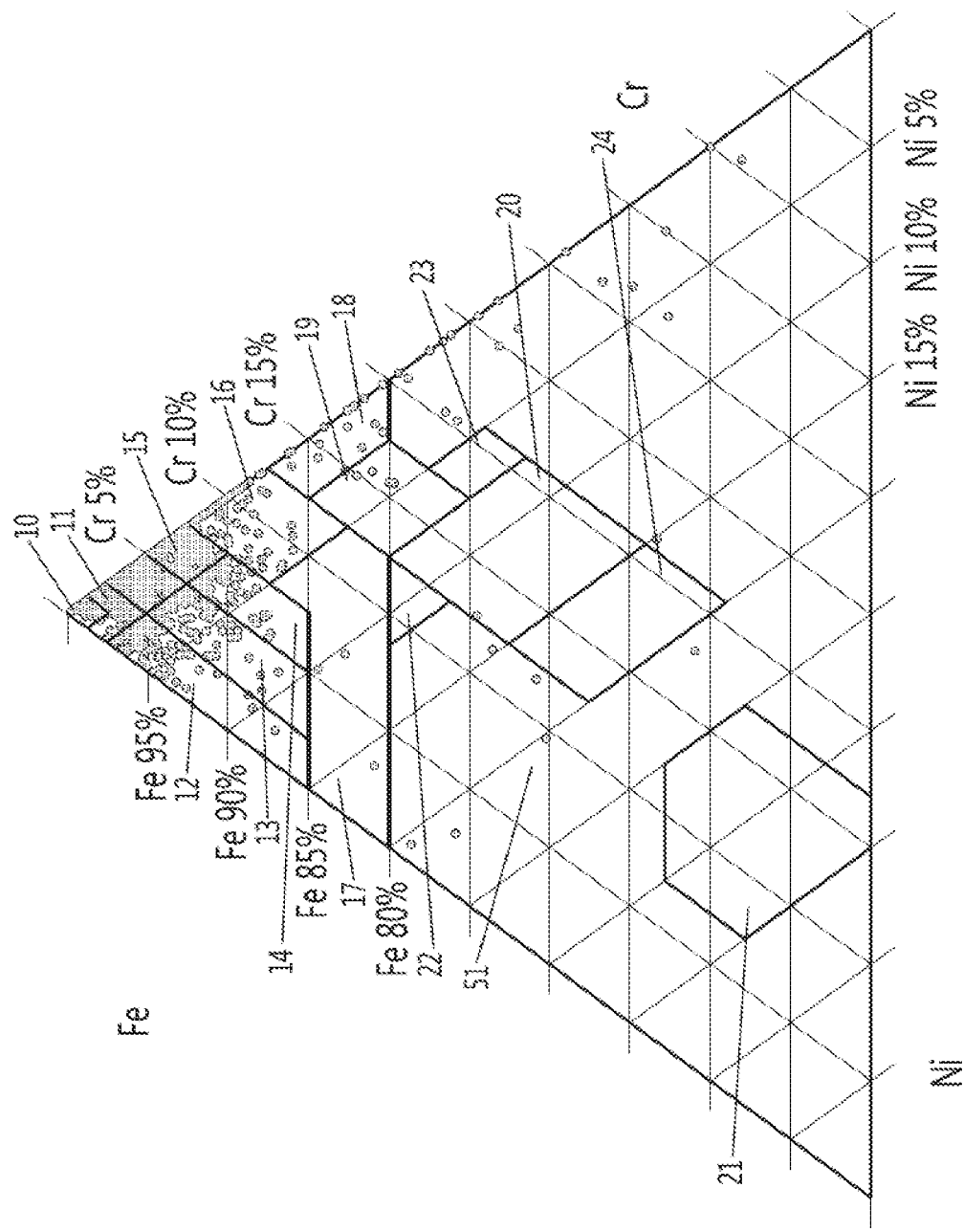
FIG. 3 illustrates an example of different alloy zones that may be used for categorizing particles.

FIG. 3 illustrates an example of how categories may be defined with respect to iron (Fe), chromium (Cr) and nickel (Ni) composition in an alloy. The diagram is divided into different zones, corresponding to different categories. Dots on the diagram illustrate how example particles 124 fall within different zones. The zones may be associated with a particular alloy and/or expected sources of the alloy. For example, zone 15 may be associated with M50, a bearing material. A particle that is categorized as belonging to the category of zone 15 may be expected to originate from a bearing, and its presence may be predictive of bearing wear and/or a failure mechanism related to bearing wear.

Categorization of each particle 124 may be carried out using an algorithm to match each particle to the appropriate category. Each particle may be compared against a historical standard for a category, in order to determine if that particle 124 belongs in that category. Example algorithms for carrying out this categorization include the use of a Cross Probability Match (CPM) Index, as well as logical exclusion tests.

The CPM may be understood as an evaluation of the product of the likelihood of the unknown particle to be the standard (PvS) and the likelihood of the standard to be the unknown particle (SvP). In this example, the likelihood of a match may be based on an evaluation of the elemental composition of the particle compared to that of a historical standard for that category or sub-category.

An example version of CPM uses a linear model, which is based on a linear contribution of each element equal to its concentration. The CPM linear model may be described by the equation:

$$CPM_{ij} = P_j v S_i \times S_i v P_j \times 100$$

where $$P_j v S_i = \sum_{k}^{n} \left( \min\left[\frac{E_{P_k}}{E_{S_k}}, \frac{E_{S_k}}{E_{P_k}}\right]^2 \times N_{S_k} \right)$$

$$S_i v P_j = \sum_{k}^{n} \left( \min\left[\frac{E_{P_k}}{E_{S_k}}, \frac{E_{S_k}}{E_{P_k}}\right]^2 \times N_{P_k} \right)$$

$$N_{P_k} = \frac{E_{P_k}}{\sum_{l}^{n}(E_{P_l})}$$

and $$N_{S_k} = \frac{E_{S_k}}{\sum_{l}^{n}(E_{S_l})}$$

and where i denotes the particle being categorized; j denotes the historical standard; n denotes the number of elements of interest used to categorize the particle; Epk denotes the concentration of the element k in the particle being categorized; Esk denotes the concentration of the element k in the historical standard being compared to; Npk denotes the normalized concentration of the element k in the particle being categorized; Nsk denotes the normalized concentration of the element k in the historical standard; Tp denotes the summation of the concentration of all elements of interest in the particle; Ts denotes the summation of the concentration of all elements of interest in the historical standard; PvS denotes the probability for the particle to be the historical standard; and SvP denotes the probability for the historical standard to be the particle.

Another example model is CPMQ, the square root version of CPM, which is based on a contribution equal to the squared of its concentration. CPMQ may be used where an element is present in a high percentage (e.g., greater than 5%) in an alloy belonging to the category of interest. The CPM square root model may be described by the equation:

$$CPMQ_{ij} = P_j v S_i^* \times S_i v P_j^* \times 100$$

where $$P_j v S_i^* = \sum_{k}^{n} \left( \min\left[\frac{E_{P_k}}{E_{S_k}}, \frac{E_{S_k}}{E_{P_k}}\right]^2 \times N_{S_k}^* \right)$$

$$S_i v P_j^* = \sum_{k}^{n} \left( \min\left[\frac{E_{P_k}}{E_{S_k}}, \frac{E_{S_k}}{E_{P_k}}\right]^2 \times N_{P_k}^* \right)$$

-continued $$N^*_{P_k} = \frac{\sqrt{E_{P_k}}}{\sum_l^n \left(\sqrt{E_{P_l}}\right)}$$

$$N^*_{S_k} = \frac{\sqrt{E_{S_k}}}{\sum_l^n \left(\sqrt{E_{S_l}}\right)}$$

Using CPM or other suitable statistic techniques to categorize each particle 124 may, for example, allow for automation of particle categorization. The use of CPM or other suitable statistical techniques may also allow for categorization of particles 124 while accounting for possible measurement noise and/or contamination, for example.

In some embodiments, a category (also referred to as a group of interest) may further break down into one or more bins defined according to particle size ranges. For example, particles 124 may be categorized in columns according to size (in μm, in the example shown) and in rows according to composition. In some embodiments, particles 124 may also be sorted into bins according to particle morphology. In some embodiments, there may be 84 categories and sub-categories. The categories may be defined based on elemental composition, alloy type, particle origin, or any other suitable category of particle characteristics and composition. Categorizing particles 124 by size, shape and/or mass, as well as composition may allow for distinguishing between one failure mechanism that is characterized by small particles 124 of a given alloy and a different failure mechanism that is characterized by large particles 124 of the same given alloy, for example. Categorizing particles 124 into categories other than simple elemental composition may also allow for discerning particle data patterns that may not be otherwise observed.

For example, a category may represent a generic type of alloy, and may include one or more levels of sub-categories that may further split the category into finer categorization, for example as precisely as the alloy unified number (UNS) of the particles analyzed. For example, a specific alloy may cover two or more categories and/or sub-categories.

Example categories and sub-categories include but are not limited to:

Environmental—sub-categories: calcium, sodium, CalSil (which may originate from cement from an airstrip), dust—earth, talc, vermiculite (which may originate from packaging of the sample) and chlorides (with further sub-category NaCl).

Metallic—sub-categories: iron (which may include further sub-categories of different composition zones such as different steels, and other alloy types), nickel, titanium, copper (with further sub-categories such as brass, bronze and leaded copper), zinc (which may originate from galvanized coating found in the engine filters and is typically found with iron and phosphorus particles also), aluminum, magnesium, cobalt and chromium.

Non-metallic—sub-categories: aluminum/silicon, silicon/aluminum, silicon/magnesium, magnesium/aluminum, fiberglass, asbestos, filter fibers, glass beads and silica.

Others—sub-categories: MoS2, grease with MoS2, lead and contaminated silver.

Plating—sub-categories: tin, silver, cadmium, copper, phosphate-manganese (AMS 2481) and chromium.

Not categorized.

These exemplary categories may be predefined based on knowledge or expectation of what kind of particles 124 would be obtained from an fluid sample 126 of a given engine type. The categories may also be defined based on the analysis of the samples. For example, if it appears that most of the particles 124 fall into a few categories, sub-categories may be defined for those few categories in order to more finely categorize the particles 124. The defined categories may be different for different engine types and/or at different total operating hours, for example.

At 225 of FIG. 2, the data obtained from categorization of particles 124 is compared with reference data 134, which may include historical data associated with the engine type (e.g., other engines, fleet data) and/or any data from previous analyses of the same engine. This comparison may be based on a quantification in each category (e.g., a count of particles of certain characteristics, such as certain size, morphology and/or mass, which may be based on the sorting of particles into bins within each category, and may include normalizing the count to a 25 mL sample and for 100% of the area analyzed), to obtain a set of categorized data. The categorized data in each category and/or sub-category, as well as categorized data representative of all categories, may be compared with the historical data.

In an example where an fluid sample 126 from an engine is being analyzed, data obtained for the specific fluid sample 126 may be compared with other historical data obtained from engines of the same or similar type obtained at equivalent or similar operating hours and/or equivalent or similar operating conditions (e.g., running in a dry or sandy environment vs. a wet environment).

Historical data may be collected as part of the disclosed methods and systems, may be collected using other techniques, may be collected as part of routine maintenance, may be derived from previous records and engine specifications, or may be obtained by any other suitable means. One or more sets of historical data may be represented by an aggregate or general historical model of expected engine wear and/or failure mechanisms for engines of a particular engine type. The historical model may be a simple average of all data for a given engine type at a given operating age, for example. In some embodiments, a historical model may include an average of all data, expunged of six-sigma results. The model may be adjusted over time as more historical data sets are added to the model. A model based on a larger population of historical data may be a more accurate and precise predictor of engine failure than a model based on a smaller population of historical data. Historical data may include data from different engines of the same engine type at the same or similar operating hours (also referred to as latitudinal data or cross-sectional data), and may also include data from the same engine at different operating hours (also referred to as longitudinal data).

The comparison between the sample data and the historical data may be carried out using any suitable statistical methods. For example, any category with sample data values that fall outside a three sigma range of the historical data may be flagged or highlighted. For example, for a given category the comparison may use the calculation: (sample data−average data)/standard deviation.

In some embodiments, a composite variation value may be calculated based on the difference between the sample and historical data, for example expressed in standard deviation and/or a weight assigned to each category. For example, a composite index for a low alloy may be calculated as:

$$Cl_{LowAlloy} = \sum_{i=10}^{12} \left[ \sum_{j=1}^{5} w_{ij} S_{ij} \right]$$

Where: i is the zone category; j is the particle size category; Sij is the deviation expressed in standard deviation for the particles of the category size j from the zone i; Wij is the weight attributed for the particles of the category size j from the zone I, and the sum of all weight is equal to 1. The weighting factor may be based on historical data and/or the engine model.

At 230, a prediction of any possible future failure(s) and/or failure mechanism(s) is generated. This prediction may be based on the results of the comparison with historical data. For example, a category flagged as being outside a three sigma range of the historical data may be considered to be predictive of failure of an engine part associated with that category. This may be based on trend analysis of analysis results from the same engine or engine type. Corrective action (e.g., engine removal or increased frequency of testing) may be determined based on the engine history and/or expected performance of the engine type, for example. In some embodiments, prediction of expected failure(s) and/or failure mechanism(s) may involve review by an expert, a technical specialist and/or an operator. Examples of predicted mechanism of failure include excess vibration, bearing wear, external contamination following engine maintenance, bearing rubbing, gear degradation, and bearing cage and race degradation, among others.

A prediction of failure may be based on a combination of two or more factors. For example, comparison results that indicate a given engine has a greater than normal number of small particles in ferrous alloy zone 20 (corresponding to stainless steel) may indicate excessive engine vibration. This result, in addition to comparison data that indicates the engine has an increased number of particles in zone 11 (corresponding to a bearing cage) and the presence of submicron particles in zone 15, may together indicate that the engine is exhibiting problems with a bearing when compared to historical data.

A particular engine type may be known to have certain failure patterns, based on historical data. By comparing data for a given engine belonging to that category/sub-category with historical data for that category/sub-category, a prediction may be generated to indicate when the given engine is expected to fail and/or the expected failure mechanism for the given engine. For example, historical data may reveal certain patterns of particle characteristics over time. By comparing the sample particle data of the given engine with the historical pattern over time, a prediction may be generated of where the given engine is in the expected timeline for engine failure.

In some embodiments, two or more engine types may share the same or similar mechanism of failure. In such cases, historical data of one engine type may be used for failure prediction of the other engine type, historical data of two or more engine types may be compiled together, and/or the sample historical data may be used for failure prediction of two or more engine types, for example.

Using the generated prediction of failure, appropriate action may be taken. For example, where failure of a particular part has been predicted, that part may be replaced and/or monitored with greater frequency. Or, where failure of the engine has been predicted, that engine may be placed on a tighter maintenance and/or oil analysis schedule. For example, the disclosed methods may include performing a maintenance or pre-maintenance action on the engine. Maintenance or pre-maintenance actions that may be performed include, for example, flagging the engine for maintenance (e.g., in a maintenance file), generating a notification to alert a user for the need to perform maintenance, scheduling maintenance for the engine, and performing the appropriate maintenance, among others. The maintenance or pre-maintenance action performed may be dependent on the generated prediction.

The generated prediction may be recorded and saved for further action and/or future reference. The results may also be added to the historical data. An electronic image of the sample may also be stored for future reference and/or further processing.

Figure 4:
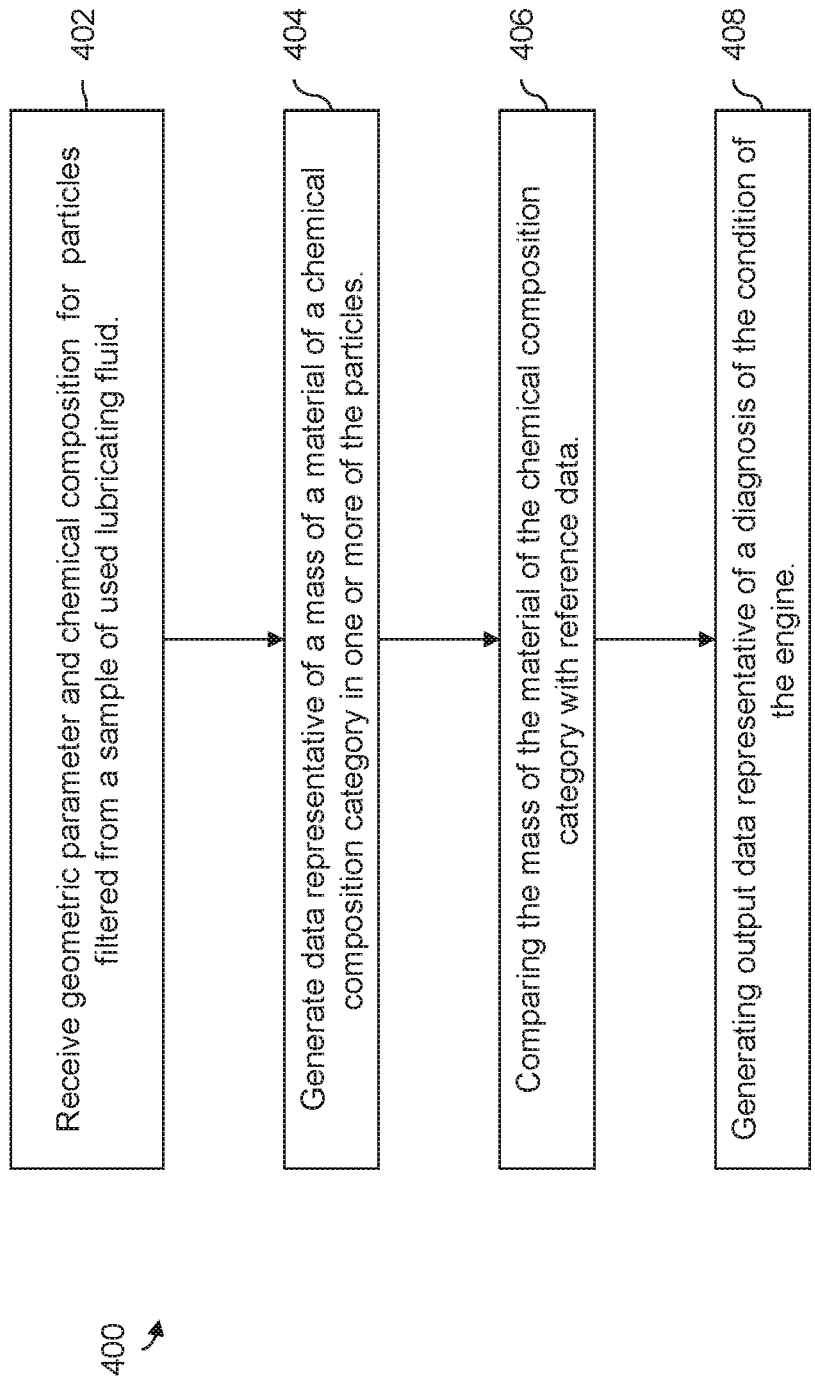
FIG. 4 is a flowchart illustrating an exemplary method for diagnosing a condition of an engine.

FIG. 4 is a flowchart illustrating method 400 for diagnosing a condition of an engine such as a gas turbine engine of an aircraft. In some embodiments, method 400 may be used to predict a failure of one or more components of the engine. Method 400 may be performed in its entirety or in part using system 10 shown in FIG. 1 and described above. Method 400 or part(s) thereof may be performed in combination with part(s) of other methods disclosed herein. Aspects of the systems and methods described above may also apply to method 400. Some or all of method 400 may be computer-implemented.

Method 400 may comprise the determination of a mass of one or more particles 124 and/or the mass of one or more elements, alloys or material types contained in one or more particles 124. The mass information in combination with a chemical composition category of a particle or a group of particles 124 filtered from lubrication fluid sample 126 may be used to diagnose a condition of engine and determine whether a (e.g., corrective) action should be initiated. For example, method 400 may provide an indication of how much mass of a particular element (e.g., Fe, Cr, Al, Ni), of a particular material type (e.g., ferrous or non-ferrous, tool steel), and/or of a particular alloy (e.g., M50) is present in sample 126 of lubricating fluid. For example, method 400 may provide an indication of how many grams (or micrograms) of a particular chemical composition category is present per liter of lubricating fluid (e.g., Iron (Fe) 0.003 µg/L, Chromium (Cr) 0.0004 µg/L, M50 0.002 µg/L, tool steel 0.005 µg/L). Performing method 400 using samples 126 of lubricating fluid obtained (i.e., collected) from an engine at different times in order to monitor the mass of one or more elements, material types or alloys in the lubricating fluid of the engine may provide an indication as to whether a particular condition (e.g., wear mechanism) is active and whether the condition is progressing. Also, since particles 124 are filtered from fluid sample 126, the information extracted from the filtered particles 124 is representative of the wear mechanisms that were active at the time the sample was obtained since the particles 124 were still in suspension in the lubricating fluid.

In various embodiments, method 400 may comprise: receiving input data 128 representative of a respective geometric parameter and a respective chemical composition for a plurality of particles 124 filtered from sample 126 of used lubricating fluid obtained from the engine (see block 402); from input data 128, generating data representative of a mass of material of a chemical composition category in one or more of the particles 124 (see block 404); comparing the mass of material of the chemical composition category with reference data 134 (see block 406); and based on the comparison, generating output data 130 representative of a diagnosis of the condition of the engine (see block 408).

As explained above, reference data 134 may comprise historical data associated with the particular engine from which lubricating fluid sample 126 was obtained and/or associated with one or more other engines (e.g., fleet data). The first chemical composition category may be representative of an element, a material type or an alloy.

The geometric parameter (or one or more geometric parameters) may be used as a basis for calculating the mass of each particle 124. It is understood that the calculation of the mass may be an estimate of the mass of particle 124 made based on the geometric parameter associated with particle 124 and, optionally, based on one or more assumptions of the overall shape of particle 124. In some embodiments, the geometric parameter may include a surface area of particle 124, a size of particle 124 and/or one or more dimensions of particle 124. Using such one or more geometric parameters, an estimation of volume of the particle 124 in question may be computed by computer 112. Alternatively, a volume of the particle 124 may be included in input data 128 in some embodiments. Using the volume of particle 124, method 400 may comprise generating data representative of a mass of material using the known density or specific gravity associated with the chemical composition category to which particle 124 has been assigned.

The mass information may also be computed taking into consideration the percent concentration of a particular element, alloy or material type in particle 124 so that the mass of material in particle 124 for a particular chemical composition category may be prorated based on the chemical composition of the particle 124. It is understood that, in some situations, a particle 124 may contain materials from more than one chemical composition category due to interactions between materials and also depending on how the chemical categories are defined (e.g., elemental, by alloy or by material type). For example, a particle 124 containing mainly stainless steel may have a concentration of about 11% chromium content by mass. Accordingly, the concentration of chromium in particle 124 may be taken into consideration when computing the mass of chromium in that particle 124. For example, for a particle having an estimated mass of 0.0034 μg and an estimated composition of tungsten (VV) of 2.0% by mass, the estimated mass of tungsten (VV) in particle 124 may be estimated to be 0.0034 μg×2.0%=0.000068 μg.

In some embodiments, the mass determined (estimated) may comprise a cumulative (total) mass of all material of a particular chemical composition category found in particles 124 of lubricating fluid sample 126.

In some embodiments, the reference data 134 may comprises predefined engine diagnosis rules obtained from a database stored in memory 118 or elsewhere and used for evaluation of the mass of material determined to diagnose the condition of the engine. Such rules may include ranges and threshold masses per volume of lubricating fluid for different chemical composition categories and which may be indicative of different conditions (e.g., wear mechanisms, failure signs) of the engine. Accordingly, comparison of the mass and composition category information with reference data 134 may be useful in diagnosing a condition of the engine. In various embodiments such method of diagnosis using mass may be conducted instead of conventional methods, or, may be conducted in conjunction with conventional methods in order to complement such conventional methods.

Figure 5A:
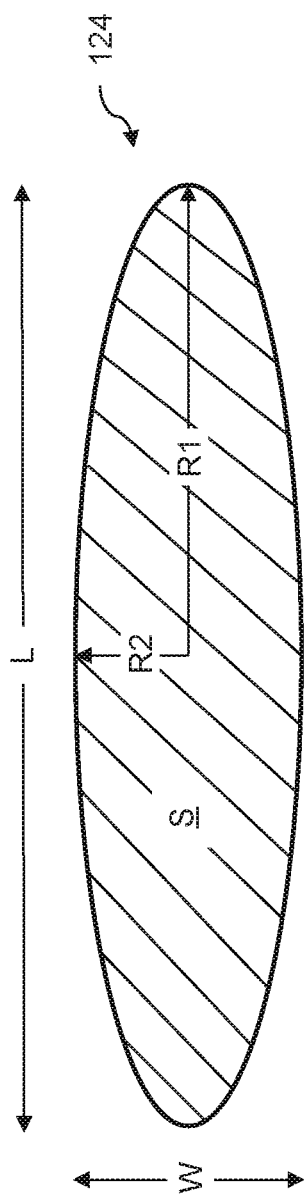
FIG. 5A shows a schematic representation of a top plan view of an exemplary approximated shape of a particle filtered from a fluid sample.
Figure 5B:
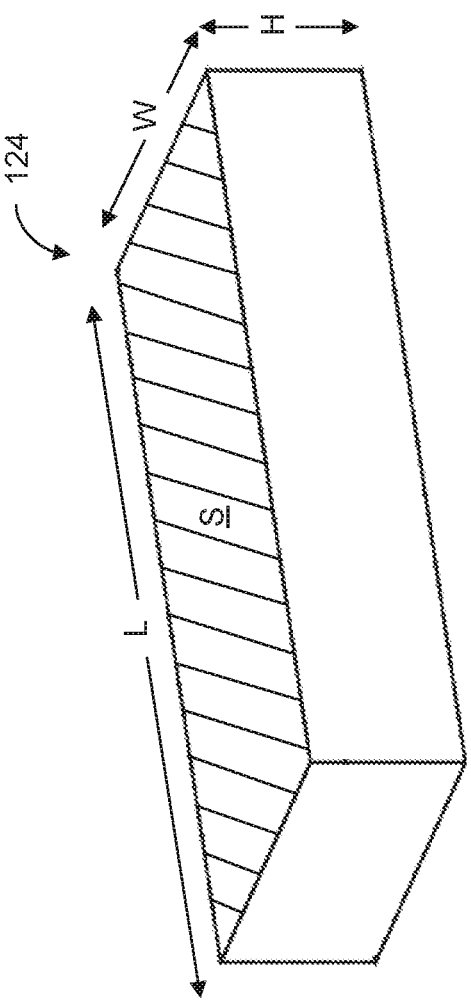
FIG. 5B shows a schematic representation of a perspective view of an exemplary approximated shape of a particle filtered from a fluid sample.

FIG. 5A shows a schematic representation of a top plan view of an exemplary approximated ellipsoid shape of particle 124 filtered from lubricating fluid sample 126. The ellipsoid shape (e.g., needle-shaped, rice grain-shaped) shown in FIG. 5A may have a length L, a width W, dimensions R1 and R2 and a height H (i.e., thickness) in the direction perpendicular to the page. FIG. 5A may also have a surface area S visible from a vantage point located above particle 124 as would be detected by data acquisition equipment 114 (e.g., SEM) for example. Width W may be smaller than length L. FIG. 5B shows a schematic representation of a perspective view of an exemplary approximated rectangular prism shape of particle 124 filtered from a lubricating fluid sample 126. The rectangular prism shape shown in FIG. 5B may have a length L, a width W and a height H. FIG. 5B may also have a surface area S visible from a vantage point located above particle 124. Width W may be smaller than length L. Surface area S for both the ellipsoid and the rectangular prism may be representative of an area of a footprint of particle 124 visible from a vantage point above particle 124 as opposed to the entire surface area surrounding particle 124. In some embodiments, surface area S may be provided in input data 128 together with one or more of width W and length L.

In some embodiments, the shapes of FIGS. 5A and 5B may be used to estimate the volume of particle 124. For example, calculation of the volume of particle 124 may be based on the assumption that particle 124 has a shape approximating an ellipsoid shape resembling that shown in FIG. 5A and/or calculation of the volume of particle 124 may be based on the assumption that particle 124 approximates a rectangular prism shape resembling that shown in FIG. 5B. In some embodiments, the approximated shape for particle 124 may be selected based on the on the geometric parameter (e.g., aspect ratio L/W) acquired in input data 128. For a rectangular prism for example, the volume may be calculated as follows: Volume=L×W×H; or Volume=S×H. For an ellipsoid for example, the volume may be calculated as follows: Volume=$\frac{4}{3}$×π×R1×R2×H/2.

The height H of particle 124 may be unknown from input data 128 but it may be assumed in some situations that the height H is less than the width W because the likelihood of particle 124 resting on its narrow side (edge) during the acquisition of input data 128 may be small. In some embodiments, it can be estimated that about 50% of particles 124 will have a shape approximating a rectangular prism and about 50% of particles 124 will have a shape approximating an ellipsoid. In some embodiments, it can be estimated that about ⅓ of particles 124 will have a height H of about 0.5 W, about ⅓ of particles 124 will have a height of about 0.25 W and the remaining ⅓ of particles 124 will have a height of about 0.1 W. According to these assumptions and the data available in input data 128, the average volume of a particle 124 may be estimated as follows: Volume=(S×0.5 W+S×0.25 W+S×0.1 W+S×0.5 W×⅔+S×0.25 W×⅔+S×0.1 W×⅔)/6. For the sake of simplicity, the calculation of the volume of particle 124 based on the assumptions made above may be reduced to: Volume=0.236 W, where W is smaller than length L. In some embodiments, the volume of particle 124 may be approximated as 0.25 W. It is understood that the above calculation of the volume of particle 124 may be based on an average distribution of the particle shape distribution. It is understood that the volume calculations could be different for different particle shapes.

In various embodiments, method 400 may comprise the acquisition of input data 128 using data acquisition equipment 114 and/or other steps disclosed herein. For example, generating input data 128 may comprise performing particle analysis using X-ray spectroscopy. For example, particles 124 may have a size between about 0.5 µm and about 1600 µm.

In some embodiments, method 400 may comprise: using a plurality of particles 124 filtered from sample 126 of used lubricating fluid obtained from the gas turbine engine, generating input data 128 representative of a respective geometric parameter and a respective chemical composition for each of the plurality of particles 124; using input data 128, generating data representative of a cumulative (i.e., total) mass of material in particles 124 in a chemical composition category; comparing the cumulative mass of material in the chemical composition category with reference data 134; and based on the comparison, generating output data 130 representative of a diagnosis of the condition of the engine.

In some embodiments, method 400 may comprise using output data 130 to initiate a corrective action such as a maintenance procedure or some recommended inspection task/schedule based on the output data. As explained above, reference data 134 may comprises predefined engine diagnosis rules obtained from a database. The initiation of such action(s) may, for example, comprise recommending to maintenance or other personnel that such action should be carried out.

Figure 6:
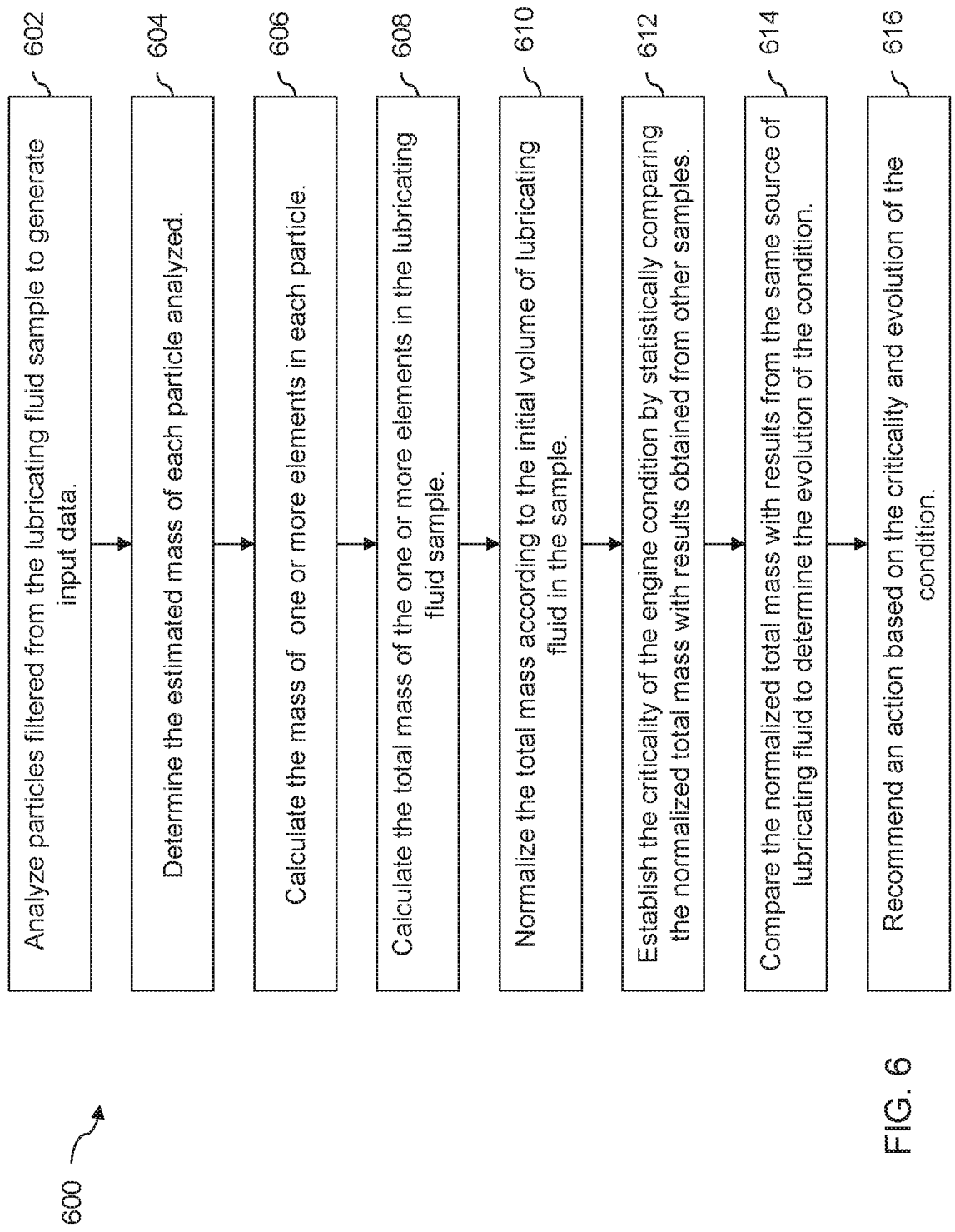
FIG. 6 is a flowchart illustrating a method for diagnosing a condition of an engine based on a total mass of one or more elements in particles in a sample of lubricating fluid.

FIG. 6 is a flowchart illustrating method 600 for diagnosing a condition of an engine such as a gas turbine engine of an aircraft based on a total mass of one or more elements in a sample 126 of lubricating fluid. Method 600 may be performed in its entirety or in part using system 10 shown in FIG. 1 and described above. Method 600 or part(s) thereof may be performed in combination with part(s) of other methods disclosed herein. Some or all of method 600 may be computer-implemented.

In various embodiments, method 600 may comprise: analyzing particles 124 filtered from lubricating fluid sample 126 to generate input data 128 (see block 602); determining the estimated mass of each particle 124 analyzed (see block 604); calculating the mass of one or more elements in each particle 124 (see block 606); calculating the total mass of the one or more elements in lubricating fluid sample 126 (see block 608); normalizing the total mass according to the initial volume of lubricating fluid in sample 126 (see block 610); establishing the criticality of the engine condition by statistically comparing the normalized total mass with results obtained from other samples (see block 612); comparing the normalized total mass with results from the same source of lubricating fluid (i.e., another sample from the same oil of the same engine) to determine the evolution of the condition (see block 614); and recommending an action based on the criticality and evolution of the condition (see block 616).

Figure 7:
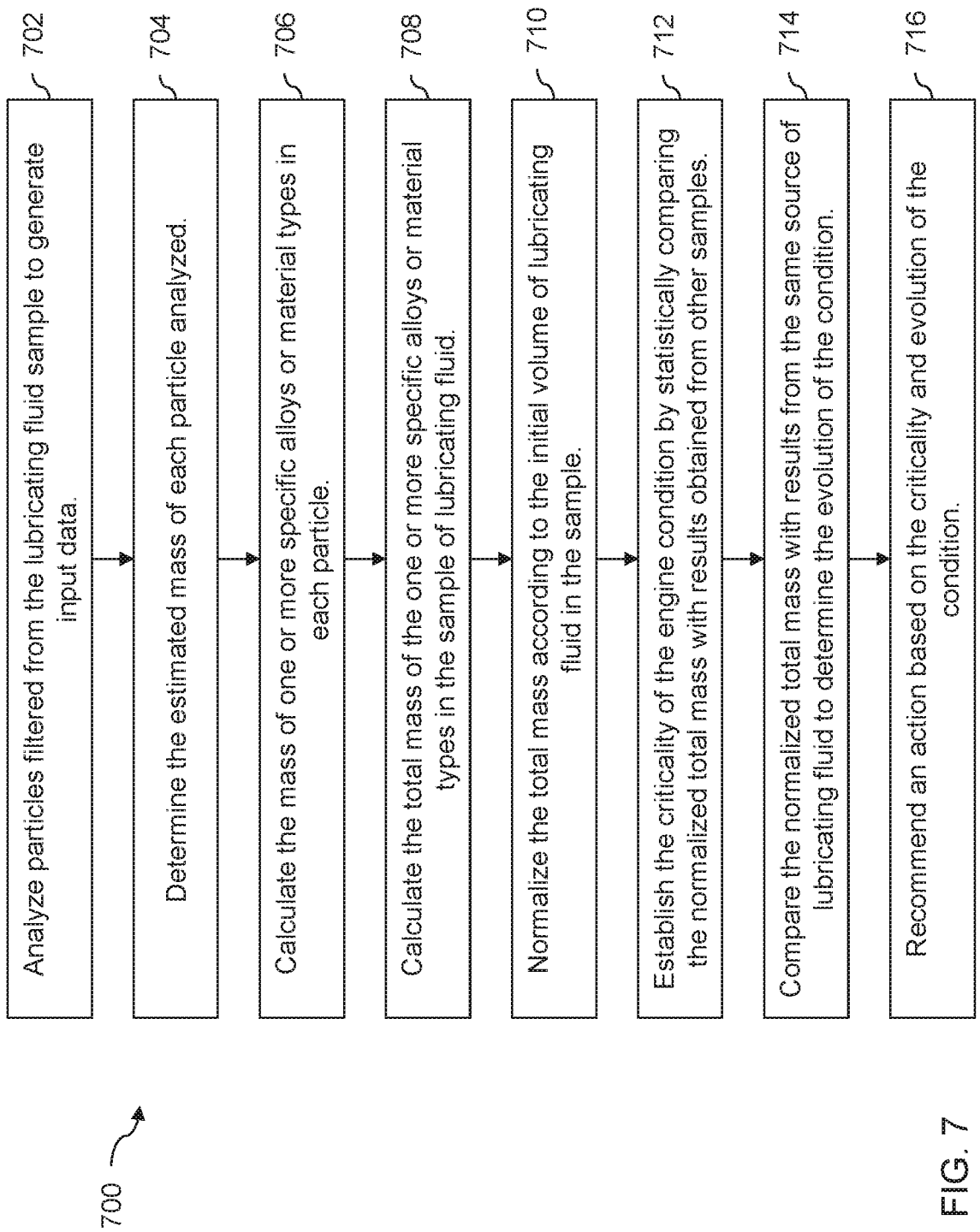
FIG. 7 is a flowchart illustrating a method for diagnosing a condition of an engine based on a total mass of one or more alloys or material types in particles in a sample of lubricating fluid.

FIG. 7 is a flowchart illustrating method 700 for diagnosing a condition of an engine such as a gas turbine engine of an aircraft based on a total mass of one or more alloys or material types in a sample 126 of lubricating fluid. Method 700 may be performed in its entirety or in part using system 10 shown in FIG. 1 and described above. Method 700 or part(s) thereof may be performed in combination with part(s) of other methods disclosed herein. Some or all of method 700 may be computer-implemented.

In various embodiments, method 700 may comprise: analyzing particles 124 filtered from lubricating fluid sample 126 to generate input data 128 (see block 702); determining the estimated mass of each particle 124 analyzed (see block 704); calculating the mass of one or more specific alloys or material types in each particle 124 (see block 706); calculating the total mass of the one or more specific alloys or material types in lubricating fluid sample 126 (see block 708); normalizing the total mass according to the initial volume of lubricating fluid in sample 126 (see block 710); establishing the criticality of the engine condition by statistically comparing the normalized total mass with results obtained from other samples (see block 712); comparing the normalized total mass with results from the same source of lubricating fluid (i.e., another sample from the same oil of the same engine) to determine the evolution of the condition (see block 714); and recommending an action based on the criticality and evolution of the condition (see block 716).

The present disclosure also provides systems for carrying out the disclosed methods. The disclosed methods and systems may allow for monitoring of an engine over time, and may allow for a timeline of expected failure mechanisms to be developed for that engine type.

The disclosed methods and systems may allow for more sensitive and/or earlier detection of possible engine failure, compared to conventional methods. For example, current oil analysis technologies may not identify the composition of each particle, and a relatively high concentration (e.g., more than 10 ppm) of wear metal in the fluid sample may be required to detect the presence of abnormal wearing. In some embodiments, the disclosed methods and systems may allow the detection limit of wear in bearing material for example to be reduced by a factor of 1000 or more, which may allow for earlier detection of a problem.

In the disclosed methods and systems, the size of the particles may also be taken into account, which may help to avoid potential error caused by the presence of one big particle. For example, a spherical particle of gear material that is 4 µm in diameter will give the same % Fe reading for the total sample as 500 particles of bearing material each 0.5 µm in diameter. If the sizes of the individual particles are not taken into account, this could lead to possible misdiagnosis of bearing wear as being gear wear.

Alternatively or in addition to particle size, the disclosed methods and systems may consider the mass of material in one or more chemical composition categories for the purpose of diagnosing a condition of an engine as described above. The use of mass may be useful in cases where the particles could contain materials from similar compositions and/or where there could be interactions between materials.

The conventional SOAP technique typically relies on elemental analysis using emission/atomic absorption analysis of particles. The particles analyzed are typically limited to 2-3 µm or smaller. The result of SOAP is typically a quantification of elements (e.g., iron) by volume (e.g., in ppm), without a consideration of particle size, mass, alloy type or shape of the particle, and may produce a relatively small number of data points (e.g., about 30 data points that describe the total quantities of individual elements in the total sample). In the present disclosure, in additional to categories defined by elemental composition, categories may be defined in other ways, such as by alloy type and expected particle origin (e.g., specific engine component that might be the source of the particle), as well as by particle size, shape and/or mass. These other category definitions may help in identifying data patterns that may not be discernible when categorizing particles only by elemental composition. Further, in some embodiments, the disclosed methods and systems may consider characteristics of each individual particle, rather than overall characteristics of the total sample.

Conventional oil analysis techniques typically are limited to analysis of relatively large particles (e.g., 30 µm or larger). The presently disclosed methods and systems may allow oil analysis to be carried out on large as well as smaller particles.

In various aspects and embodiments, the present disclosure may provide the ability to identify the composition and mass of wear material in a lubricating fluid sample. In some embodiments, the disclosed methods and systems may provide a low detection limit that may allow the detection of abnormal wearing sufficiently early in the deterioration cycle, giving a chance to fix the problem during a planned maintenance. Early and/or rapid detection of a problem may also give the opportunity to fix the root cause of the problem early, which may help to reduce the total number of problematic engines in the field.

The above description is meant to be exemplary only, and one skilled in the art will recognize that changes may be made to the embodiments described without departing from the scope of the invention disclosed. For example, although the disclosed method has been described in terms of a number of steps, certain steps may be omitted and/or rearranged in order. Although the present disclosure makes reference to oil analysis for predicting failure in an engine, analysis of other fluids (e.g., other lubricants) for failure prediction in other components may be carried out using the disclosed methods and systems. The present disclosure is also intended to cover and embrace all suitable changes in technology. Still other modifications which fall within the scope of the present invention will be apparent to those skilled in the art, in light of a review of this disclosure, and such modifications are intended to fall within the appended claims. Also, the scope of the claims should not be limited by the preferred embodiments set forth in the examples, but should be given the broadest interpretation consistent with the description as a whole.

REFERENCES

[1] M. Lukas, D. P. Anderson, Spectro Incorporated, Littleton, Mass. "Rotrode Filter Spectroscopy, Does It have a Place in Commercial or Military Oil Analysis Laboratory".
[2] K. J. Eisentraut, R. W. Newman, C. S. Saba, R. E. Kauffman, and W. E. Rhine, "Spectrometrix oil analysis: detecting engine failures before they occur", Analytical Chemistry 56, August 84, 1086A-1094A.
[3] R. R. Whitlock, Advances in X-Ray Analysis, Volume 40, 1996.

What is claimed is:

1. A method for diagnosing a condition of an engine, the method comprising:
   receiving a plurality of particles from lubricating fluid of the engine;
   obtaining, using data acquisition equipment, input data associated with the plurality particles, the input data representative of a respective volume of and a respective chemical composition category for each of the plurality of particles;
   using one or more data processors:
      from the input data, generating data representative of a mass of material of a selected one of the chemical composition categories in the plurality of particles by using the respective volumes of the particles in the selected chemical composition category and a density of the selected chemical composition category;
      comparing the mass of material of the selected chemical composition category in the plurality of particles with reference data; and
      based on the comparison, generating output data representative of a diagnosis of the condition of the engine.

2. The method as defined in claim 1, wherein the reference data comprises historical data associated with the engine or historical data associated with one or more other engines.

3. The method as defined in claim 1, wherein the selected chemical composition category is representative of an element.

4. The method as defined in claim 1, wherein the selected chemical composition category is representative of a material type.

5. The method as defined in claim 1, wherein the selected chemical composition category is representative of an alloy.

6. The method as defined in claim 1, comprising computing the volume of at least one of the particles by computing a volume of an ellipsoid or of rectangular prism.

7. The method as defined in claim 1, wherein the mass of material is a cumulative mass of all the material of the selected chemical composition category in the plurality of particles.

8. The method as defined in claim 1, wherein the reference data comprises predefined engine diagnosis rules obtained from a database.

9. The method as defined in claim 1, wherein generating data representative of the mass of material includes prorating a mass of the particles in the selected chemical composition category based on a chemical composition of the particles in the selected chemical composition category.

10. A system for diagnosing a condition of an engine, the system comprising one or more data processors and one or more memory(ies) containing machine-readable instructions for execution by the one or more data processors, the machine-readable instructions being configured to cause the one or more data processors to carry out the method performed by the one or more processors of claim 1.

11. A non-transitory computer-readable medium or media embodying computer-executable instructions configured for causing one or more data processors to carry out the method performed by the one or more processors of claim 1.

12. A method for diagnosing a condition of a gas turbine engine, the method comprising:
   receiving a plurality of particles from lubricating fluid of the gas turbine engine;
   using the plurality of particles, generating input data representative of a respective volume of and a respective chemical composition category for each of the plurality of particles;
   using the input data and a density of a selected one of the chemical composition categories, computing a cumulative mass of material of the selected chemical composition category in the plurality of particles;
   comparing the cumulative mass of material of the selected chemical composition category with reference data; and
   based on the comparison, generating output data representative of a diagnosis of the condition of the engine.

13. The method as defined in claim 12, comprising using the output data to initiate a corrective action.

14. The method as defined in claim 12, wherein the reference data comprises predefined engine diagnosis rules obtained from a database.

15. The method as defined in claim 12, wherein the particles have a size between 0.5 μm and 1600 μm.

* * * * *